(12) United States Patent
Prasad et al.

(10) Patent No.: US 10,994,193 B1
(45) Date of Patent: *May 4, 2021

(54) SYSTEM, METHOD AND APPARATUS FOR COLLECTING AND UTILIZING BIG DATA FOR ONLINE GAMEPLAY

(71) Applicant: United Services Automobile Association, San Antonio, TX (US)

(72) Inventors: Bharat Prasad, San Antonio, TX (US); Christine Marie Brown, Helotes, TX (US); Rod Gonzales, San Antonio, TX (US); Jodi Jean Healy, Johns Creek, GA (US)

(73) Assignee: United Services Automobile Association, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/593,670

(22) Filed: Oct. 4, 2019

Related U.S. Application Data

(60) Continuation of application No. 15/921,417, filed on Mar. 14, 2018, now Pat. No. 10,471,342, which is a division of application No. 14/942,036, filed on Nov. 16, 2015, now Pat. No. 9,943,754.

(60) Provisional application No. 62/079,656, filed on Nov. 14, 2014.

(51) Int. Cl.
| | |
|---|---|
| *A63F 13/212* | (2014.01) |
| *A63F 13/92* | (2014.01) |
| *A63F 13/32* | (2014.01) |
| *A63F 13/25* | (2014.01) |
| *A61B 5/0205* | (2006.01) |
| *A63F 13/33* | (2014.01) |
| *A63F 13/35* | (2014.01) |
| *A61B 5/01* | (2006.01) |
| *A61B 5/024* | (2006.01) |
| *G16H 50/20* | (2018.01) |
| *A61B 5/021* | (2006.01) |
| *A61B 5/08* | (2006.01) |

(52) U.S. Cl.
CPC .............. *A63F 13/212* (2014.09); *A61B 5/01* (2013.01); *A61B 5/02055* (2013.01); *A63F 13/25* (2014.09); *A63F 13/32* (2014.09); *A63F 13/33* (2014.09); *A63F 13/35* (2014.09); *A63F 13/92* (2014.09); *A61B 5/021* (2013.01); *A61B 5/024* (2013.01); *A61B 5/0816* (2013.01); *G16H 50/20* (2018.01)

(58) Field of Classification Search
None
See application file for complete search history.

(56) References Cited

U.S. PATENT DOCUMENTS

| | | |
|---|---|---|
| 6,226,570 B1 | 5/2001 | Hahn |
| 6,384,834 B1 | 5/2002 | Watanabe |
| 6,823,243 B2 | 11/2004 | Chinnadurai et al. |

(Continued)

*Primary Examiner* — Kevin Y Kim
(74) *Attorney, Agent, or Firm* — Locke Lord LLP; Christopher J. Capelli

(57) ABSTRACT

A system, method and apparatus for capturing data from a plurality of users for providing online gameplay based on captured user sensor data. User sensor data is captured from a plurality of sensor capture devices relative to an associated user so as to be transmitted to a gameplay server. The gameplay server executes instructions to generate a user interface on a user's client computing device for providing gameplay on each user client portable computing device utilizing, and pertinent to, the captured sensor data.

15 Claims, 3 Drawing Sheets

(56) References Cited

U.S. PATENT DOCUMENTS

| | | |
|---|---|---|
| 2010/0004791 A1 | 1/2010 | West et al. |
| 2010/0042453 A1 | 2/2010 | Scaramellino et al. |
| 2010/0174419 A1 | 7/2010 | Brumfield et al. |
| 2011/0195701 A1 | 8/2011 | Cook et al. |
| 2013/0145482 A1 | 6/2013 | Ricci et al. |
| 2014/0067296 A1 | 3/2014 | Caldeira et al. |
| 2014/0213238 A1 | 7/2014 | Giraud et al. |

SYSTEM, METHOD AND APPARATUS FOR COLLECTING AND UTILIZING BIG DATA FOR ONLINE GAMEPLAY

CROSS REFERENCE TO RELATED APPLICATIONS

This application is a Continuation of U.S. patent application Ser. No. 15/921,417 filed Mar. 14, 2018 which is incorporated herein by reference in its entirety.

FIELD OF THE INVENTION

The present invention relates generally to electronic commerce and, more particularly, to a system and method for utilizing captured big data for online gameplay.

BACKGROUND OF THE INVENTION

Electronic online games have become a growing part of the entertainment industry. More recently, such games have been provided for wireless communication devices, especially for mobile phones. Mobile phone games are available at varying levels of complexity depending upon, in particular, the bandwidth available and processing capabilities of the mobile phone itself. Such games permit a user to interact with a virtual environment. The virtual environment generally is maintained and operated by a remote device, typically a server. The user interacts with the virtual world through his/her mobile phone, which also provides the user with a window into the virtual environment, by text message, images, sounds or any combination thereof. Multiple users may interact with the virtual world, the activity of one user affecting the virtual environment for others.

SUMMARY OF THE INVENTION

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

To achieve these and other advantages and in accordance with the purpose of the illustrated embodiments, in one aspect, a system, method and apparatus for capturing data from a plurality of users for providing online gameplay based on captured user sensor data is described in which user sensor data is captured from a plurality of sensor capture devices relative to an associated user so as to be transmitted to a gameplay server. The gameplay server executes instructions to generate a user interface on a user's client computing device for providing gameplay on each user client portable computing device utilizing, and pertinent to, the captured sensor data.

BRIEF DESCRIPTION OF THE DRAWINGS

The accompanying appendices and/or drawings illustrate various non-limiting, example, inventive aspects in accordance with the present disclosure.

DETAILED DESCRIPTION OF CERTAIN EMBODIMENTS

Figure 1:
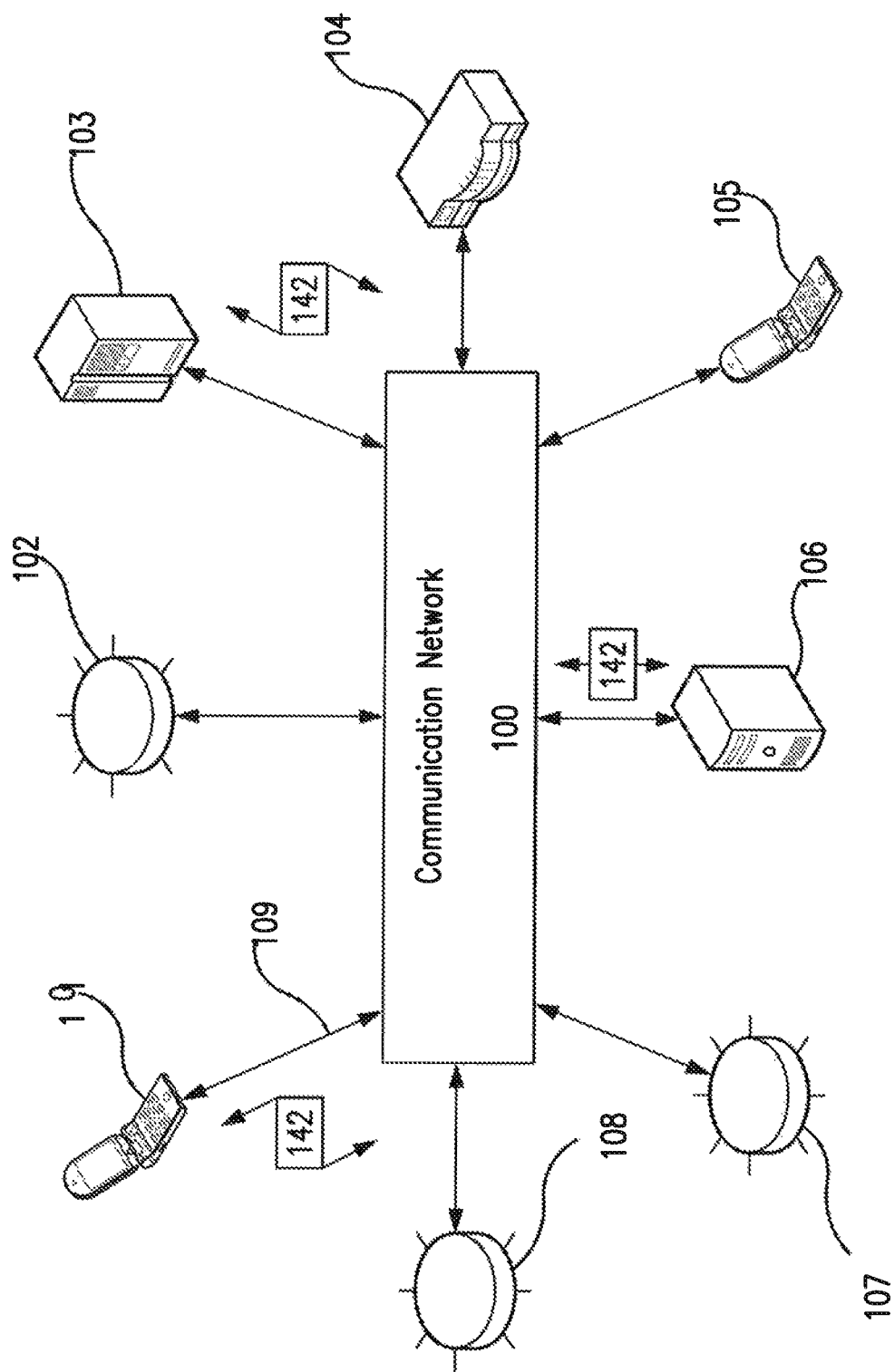
FIG. 1 illustrates an example communication network.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the illustrated embodiments, exemplary methods and materials are now described.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below are preferably a software algorithm, program or code residing on computer useable medium having control logic for enabling execution on a machine having a computer processor. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine. The embodiments described herein include such software to implement the equations, relationships and algorithms described above. One skilled in the art will appreciate further features and advantages of the illustrated embodiments based on the above-described embodiments. Accordingly, the illustrated embodiments are not to be limited by what has been particularly shown and described, except as indicated by the appended claims.

Turning now descriptively to the drawings, in which similar reference characters denote similar elements throughout the several views, FIG. 1 depicts an exemplary communications network 100 in which below illustrated embodiments may be implemented.

It is to be understood a communication network 100 is a geographically distributed collection of nodes interconnected by communication links and segments for transporting data between end nodes, such as personal computers, work stations, smart phone devices, tablets, televisions, sensors and or other devices such as automobiles, etc. Many types of networks are available, with the types ranging from local area networks (LANs) to wide area networks (WANs). LANs typically connect the nodes over dedicated private communications links located in the same general physical location, such as a building or campus. WANs, on the other hand, typically connect geographically dispersed nodes over long-distance communications links, such as common carrier telephone lines, optical lightpaths, synchronous optical networks (SONET), synchronous digital hierarchy (SDH) links, or Powerline Communications (PLC), and others.

FIG. 1 is a schematic block diagram of an example communication network 100 illustratively comprising nodes/devices 101-108 (e.g., sensors 102, client computing devices 103, device 104, smart phone devices 105, web servers 106, routers 107, switches 108, and the like) interconnected by various methods of communication. For instance, the links 109 may be wired links or may comprise a wireless communication medium, where certain nodes are in communication with other nodes, e.g., based on distance, signal strength, current operational status, location, etc. Moreover, each of the devices can communicate data packets (or frames) 142 with other devices using predefined network communication protocols as will be appreciated by those skilled in the art, such as various wired protocols and wireless protocols etc., where appropriate. In this context, a protocol consists of a set of rules defining how the nodes interact with each other. Those skilled in the art will understand that any number of nodes, devices, links, etc. may be used in the computer network, and that the view shown herein is for simplicity. Also, while the embodiments are shown herein with reference to a general network cloud, the description herein is not so limited, and may be applied to networks that are hardwired.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 2:
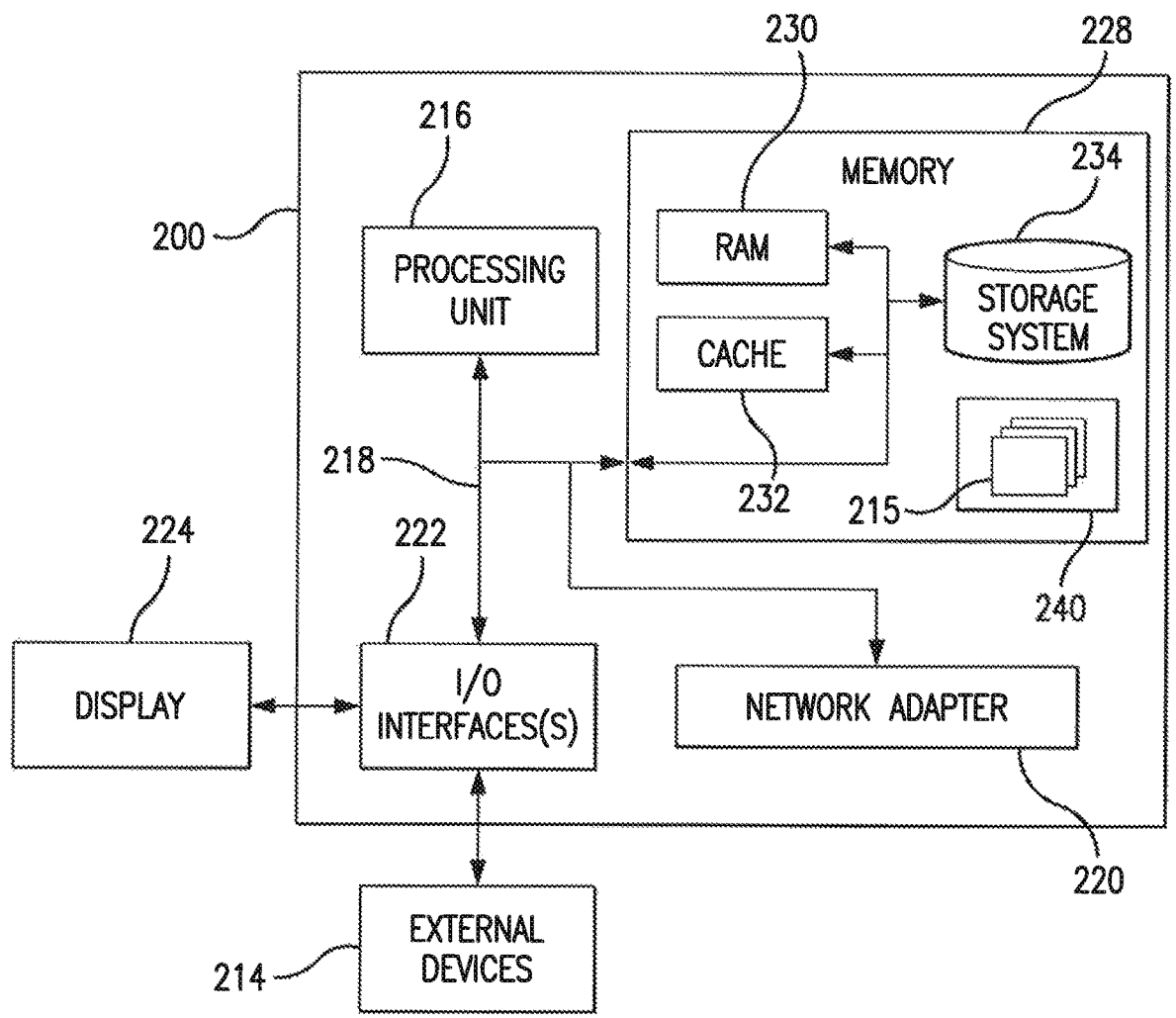
FIG. 2 illustrates an example network device/node.

FIG. 2 is a schematic block diagram of an example network computing device 200 (e.g., client computing device 103, server 106, etc.) that may be used (or components thereof) with one or more embodiments described herein, e.g., as one of the nodes shown in the network 100. As explained above, in different embodiments these various devices are configured to communicate with each other in any suitable way, such as, for example, via communication network 100.

Device 200 is intended to represent any type of computer system capable of carrying out the teachings of various embodiments of the present invention. Device 200 is only one example of a suitable system and is not intended to suggest any limitation as to the scope of use or functionality of embodiments of the invention described herein. Regardless, computing device 200 is capable of being implemented and/or performing any of the functionality set forth herein.

Computing device 200 is operational with numerous other general purpose or special purpose computing system environments or configurations. Examples of well-known computing systems, environments, and/or configurations that may be suitable for use with computing device 200 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, and distributed data processing environments that include any of the above systems or devices, and the like.

Computing device 200 may be described in the general context of computer system-executable instructions, such as program modules, being executed by a computer system. Generally, program modules may include routines, programs, objects, components, logic, data structures, and so on that perform particular tasks or implement particular abstract data types. Computing device 200 may be practiced in distributed data processing environments where tasks are performed by remote processing devices that are linked through a communications network. In a distributed data processing environment, program modules may be located in both local and remote computer system storage media including memory storage devices.

Device 200 is shown in FIG. 2 in the form of a general-purpose computing device. The components of device 200 may include, but are not limited to, one or more processors or processing units 216, a system memory 228, and a bus 218 that couples various system components including system memory 228 to processor 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing device 200 typically includes a variety of computer system readable media. Such media may be any available media that is accessible by device 200, and it includes both volatile and non-volatile media, removable and non-removable media.

System memory 228 can include computer system readable media in the form of volatile memory, such as random access memory (RAM) 230 and/or cache memory 232. Computing device 200 may further include other removable/non-removable, volatile/non-volatile computer system storage media. By way of example only, storage system 234 can be provided for reading from and writing to a non-removable, non-volatile magnetic media and/or Solid State Drives (SSD) (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 215, such as underwriting module, may be stored in memory 228 by way of example, and not limitation, as well as an operating system, one or more application programs, other program modules, and program data. Each of the operating system, one or more application programs, other program modules, and program data or some combination thereof, may include an implementation of a networking environment. Program modules 215 generally carry out the functions and/or methodologies of embodiments of the invention as described herein.

Device 200 may also communicate with one or more external devices 214 such as a keyboard, a pointing device, a display 224, etc.; one or more devices that enable a user to interact with computing device 200; and/or any devices (e.g., network card, modem, etc.) that enable computing device 200 to communicate with one or more other computing devices. Such communication can occur via Input/Output (I/O) interfaces 222. Still yet, device 200 can communicate with one or more networks such as a local area network (LAN), a general wide area network (WAN), and/or a public network (e.g., the Internet) via network adapter 220. As depicted, network adapter 220 communicates with the other components of computing device 200 via bus 218. It should be understood that although not shown, other hardware and/or software components could be used in conjunction with device 200. Examples, include, but are not limited to: microcode, device drivers, redundant processing units, external disk drive arrays, RAID systems, tape drives, and data archival storage systems, etc.

FIGS. 1 and 2 are intended to provide a brief, general description of an illustrative and/or suitable exemplary environment in which embodiments of the below described present invention may be implemented. FIGS. 1 and 2 are exemplary of a suitable environment and are not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

Figure 3:
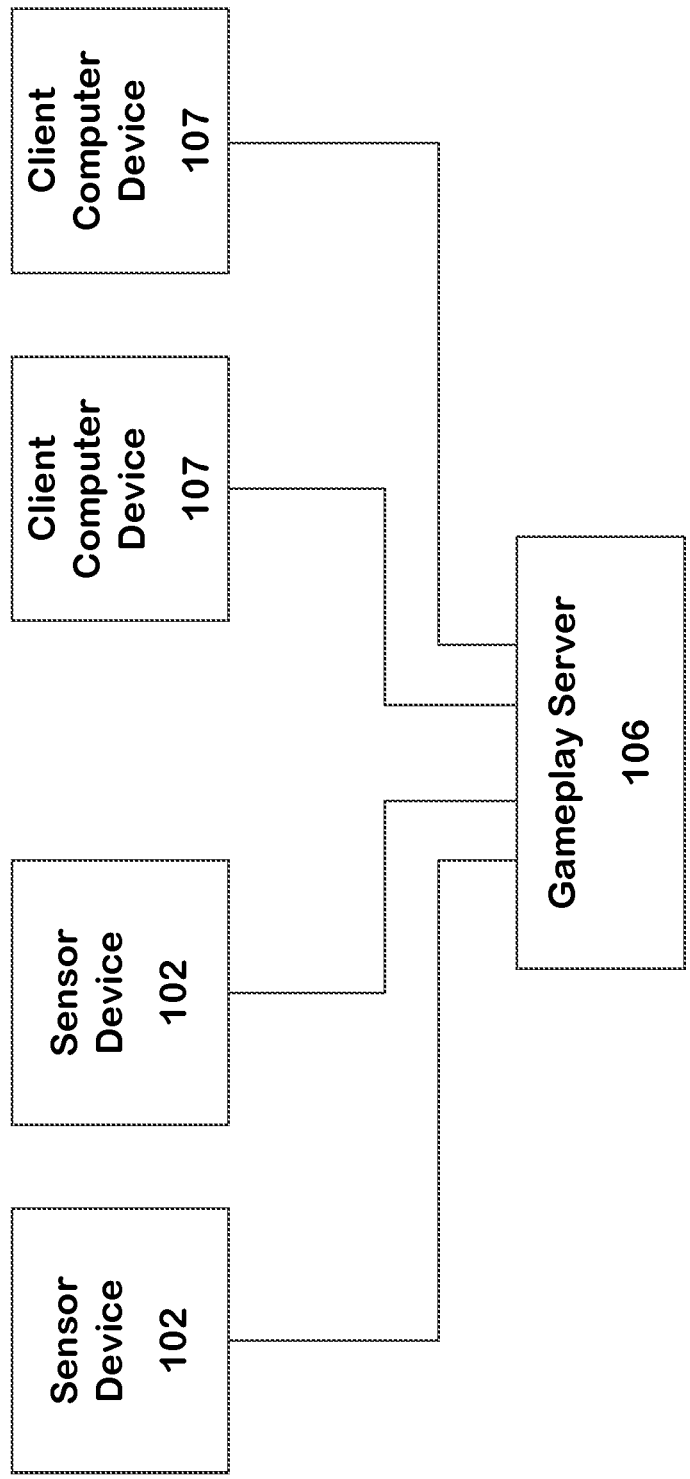
FIG. 3 illustrates a system level diagram of an illustrated embodiment utilizing the networks of FIGS. 1 and 2.

With the exemplary communication network 100 (FIG. 1) and computing device 200 (FIG. 2) being generally shown and discussed above, description of certain illustrated embodiments of the present invention will now be provided. With reference now to FIG. 3, shown is a generalized system 300 having a gameplay server 106 for acquiring real world data from sensor capture devices 102 associated with a plurality of users for creating online (internet) gameplay. Examples of gameplay scenarios are discussed below, which includes (and is not limited to) gameplay based upon user diet consumption; user energy consumption/efficiency; user health and user vehicle driving premised upon telematics data.

The sensor devices 102 used to collect the "big data" for the aforesaid gameplay may consist of any known device that is capable of collecting the required data and transmitting the captured data to the gameplay server 106 (e.g., a smart phone device, such an as iPhone™) or a device (e.g., a smart watch or other body wearable sensor device) capable of capturing required data for a gameplay (e.g., a user's heartrate) and sending the captured data to an intermediate device (e.g., a smartphone) for subsequent transmission to the gameplay server 106, preferably via a network 100. Illustrative examples of such sensor devices 106 include (and are not limited to): smart phone and tablet devices; wearable computing devices (e.g., smart watches; body sensors, clothing sensors; cameras and other suitable computing devices); energy measuring devices (e.g., electricity, water, gas, oil, etc.); telematics devices (e.g., OBD type II devices), GPS receiver and other suitable computing devices capable of acquiring suitable data relating to a user. Also shown in FIG. 3, are user computing devices 107 which communicate with the gameplay server 106 (preferably via network 100) to facilitate the gameplay to the user. Examples of such devices include (and are not limited to) smart phone and tablet devices; desktop and laptop computer devices and any other suitable computing device capable of enabling the generated gameplay of server 106. It is to be appreciated that while FIG. 2 illustrates only first and second captures devices 102 and user computing devices 107, this is done for ease of illustration purposes only, as the present illustrated embodiment is intended for a plurality of users requiring a plurality of sensor capture devices 102 and user computing devices 107, and is thus not limited be restricted to what is shown in FIG. 3.

The gameplay server 106 is configured and operational to execute instructions to generate, or interact with, a user interface on a remote user's client computing device 107 for providing gameplay on each user client portable computing device utilizing the captured data from the user sensor capture devices 102. Examples of such gameplay scenarios include (and are not limited to): user dietary user consumption wherein gameplay relates to comparing the diet of a first user with at least a second user. For instance, gameplay could include who consumes closest to targeted daily calorie consumption and/or who consumes a diet with the least sodium and/or saturated fat content. Another such gameplay scenario may include user energy consumption wherein gameplay relates to comparing the energy consumption of a first user with energy consumption of at least a second user. For instance, gameplay could include comparing periodic energy consumption of a dwelling associated with a first user with periodic energy consumption of a dwelling associated with at least a second user. Examples of such energy consumption may include one or more of: electrical power consumption, water consumption, gas consumption and oil consumption, and the like. Yet another such gameplay scenario may include user health data wherein gameplay relates to comparing the health data of a first user with the health data of at least a second user. For instance, gameplay could include comparing human body vital signs associated with a first user with human body vital signs associated with at least a second user. Examples of such human body vital signs include body temperature; blood pressure; heart rate and breathing rate, and the like.

Yet still another such gameplay scenario may include user telematics data wherein gameplay relates to comparing the telematics data of a first user with the telematics data of at least a second user. For instance, gameplay includes comparing telematics data associated with a first user with telematics data associated with at least a second user involving one or more of vehicle acceleration; vehicle braking and driving time to determine who is the safest driver and/or who is the most efficient driver. Captured telematics data may further include vehicle speed obtained from the VSS (vehicle speed sensor). Telematics gameplay may further includes comparing the phone usage (which may include overall time spent using a phone, or time spent using one or more predetermined applications) of a one driver against another driver while each driver is operating a vehicle.

Still further, another gameplay scenario may include the user comparing their game play data against themselves over time, enabling the user to rack their progress and compete against themselves.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A system for providing online gaming with data associated with a plurality of users, comprising:
   a plurality of wearable capture devices for capturing dietary consumption data from a plurality of users, wherein each capture device comprises a sensory device for capturing dietary data relative to an associated user;
   a plurality of smart devices each being communicatively coupled to one or more of the plurality of wearable capture devices configured to receive captured dietary consumption data;
   a gameplay server communicatively coupled to the plurality of smart devices for receiving the captured dietary consumption data from the plurality of users, the gameplay server including:
   a memory configured to store instructions; and
   a processor operable to execute instructions to generate a user interface on the plurality of smart devices for providing gameplay regarding the captured dietary consumptions regarding two or more users.

2. The system as recited in claim 1, wherein the captured dietary consumption data relates to calorie consumption and the gameplay includes comparing a daily calorie consumption regarding the two or more users.

3. The system as recited in claim 1, wherein the captured dietary consumption data relates to sodium consumption and the gameplay includes comparing a daily sodium consumption regarding the two or more users.

4. The system as recited in claim 1, wherein the captured dietary consumption data relates to saturated fat consumption and the gameplay includes comparing a saturated fat consumption regarding the two or more users.

5. The system as recited in claim 1, wherein the gameplay further includes comparing periodic energy consumption of a dwelling associated with the two or more users.

6. The system as recited in claim 5, further including a plurality of energy capture devices for capturing energy consumption data from a plurality of dwellings associated with the plurality of users.

7. The system as recited in claim 6, wherein the captured energy consumption includes at least one of: electrical power consumption, water consumption, gas consumption and oil consumption.

8. The system as recited in claim 1, wherein one or more of the plurality of smart devices consist of a cellular phone device.

9. The system as recited in claim 1, wherein one or more of the plurality of smart devices consist of a cellular watch device.

10. A method for providing online gaming with data associated with a plurality of users, comprising:
   capturing energy consumption data from one or more energy capture devices from a plurality of dwellings wherein each dwelling is associated with a user, and each energy capture device comprises a sensory device for capturing energy consumption data from a dwelling associated with a user;
   capturing dietary consumption data from one or more dietary capture devices associated with a user;
   generating a user interface on a remote user's client computing device;
   providing gameplay on each user client portable computing device in the generated user interface utilizing the captured energy consumption data and the captured dietary consumption data wherein the gameplay relates to determining measured energy of a dwelling and dietary consumption associated with one of the plurality of users so as to compare the determined measured energy and dietary consumption of each user's dwelling against one another.

11. The method as recited in claim 10, wherein the gameplay includes comparing periodic energy consumption of a dwelling associated with a first user with periodic energy consumption of a dwelling associated with at least a second user.

12. The method as recited in claim 10, wherein the measured energy consumption includes at least one of: electrical power consumption, water consumption, gas consumption and oil consumption.

13. The method as recited in claim 10, wherein a data capture device associated with at least one of the first user and at least second user is a smart phone device.

14. The method as recited in claim 10, wherein a data capture device associated with at least one of the first user and at least second user is a wearable computing device.

15. The method as recited in claim 10, wherein a cellular network links the one or more capture devices to the gameplay server.

* * * * *